United States Patent [19]

Luciani

[11] Patent Number: 4,997,969

[45] Date of Patent: Mar. 5, 1991

[54] CARBAMATE ADDITIVES FOR LUBRICATING COMPOSITIONS

[75] Inventor: Carmen V. Luciani, Wickliffe, Ohio

[73] Assignee: The Lubrizol Corporation, Wickliffe, Ohio

[21] Appl. No.: 283,404

[22] Filed: Dec. 12, 1988

[51] Int. Cl.$^5$ ............................................. C07C 333/00
[52] U.S. Cl. ................................... 558/240; 252/47.5
[58] Field of Search ..................... 558/240; 252/47.5

[56] References Cited

U.S. PATENT DOCUMENTS

| | | | |
|---|---|---|---|
| 2,535,877 | 9/1947 | Stewart | 558/240 |
| 2,710,872 | 6/1955 | Thompson | 558/240 |
| 2,786,866 | 3/1957 | Hook et al. | 558/240 |
| 3,089,887 | 5/1963 | Metivier | 558/240 |
| 3,833,496 | 9/1974 | Malec | 252/34 |
| 3,890,363 | 6/1975 | Malec | 252/34 |
| 3,950,534 | 4/1976 | Yagihara et al. | 558/240 |
| 4,064,265 | 12/1977 | Varsanyi et al. | 424/300 |
| 4,202,832 | 5/1980 | Fischer et al. | 544/160 |
| 4,254,142 | 3/1981 | Anderson et al. | 424/300 |
| 4,758,362 | 7/1988 | Butke | 252/47.5 |

FOREIGN PATENT DOCUMENTS 1178417 1/1963 Fed. Rep. of Germany .
1200491 6/1967 United Kingdom .

OTHER PUBLICATIONS

M. Kamel et al., "Creation of Reactive Centres on Cotton III. Synthesis of Some New Metylolacrylamide Derivatives", *Kolorisziikai Erteslio*, vol. 17, No. 7–8, 1975, pp. 217–224.

N. Kreutzkamp et al., "Synthesen von Dithiourethanen Durch Anlagerungsreaktionen", *Archiv Der Pharmazie*, vol. 304, No. 7, Jul. 1971, pp. 477–481.

Primary Examiner—Jacqueline V. Howard
Attorney, Agent, or Firm—Robert A. Franks; Frederick D. Hunter; Forrest L. Collins

[57] ABSTRACT

Compounds which improve extreme pressure and anti-wear properties of lubricating compositions are described. The compounds include the compounds of the following formula as well as statistical mixtures of those compounds:

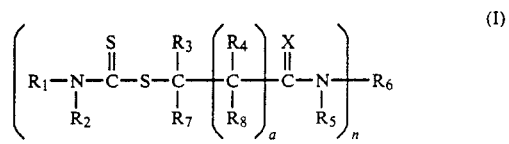

wherein $R_1$ is hydrogen or hydrocarbyl; $R_2$ is hydrocarbyl having at least 4 carbon atoms or together with $R_1$ forms a heterocyclic radical,
wherein $R_3$, $R_4$, $R_7$ and $R_8$ are each independently hydrogen or alkyl;
wherein $a$ is 0 or 1;
wherein $n$ is 1, 2 or 3;
wherein X is oxygen or sulfur;
wherein $R_5$ is hydrogen or hydrocarbyl; and
when n is 1, $R_6$ is selected from the group consisting of

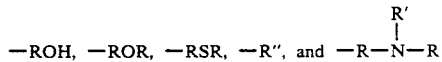

and when n is 2, $R_6$ is selected from the group consisting of

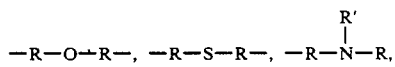

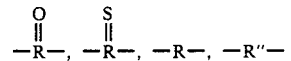

and when n is 3, $R_6$ is

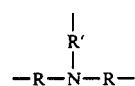

wherein R is independently an alkyl moiety, alkylene or alkylidene moiety containing 1 to 12 carbon atoms, R' is hydrogen or alkyl moiety, alkylene, alkylidene or carboxyl containing 1 to 60 carbon atoms, and R'' is aryl or substituted aryl.

12 Claims, No Drawings

CARBAMATE ADDITIVES FOR LUBRICATING COMPOSITIONS

TECHNICAL FIELD OF THE INVENTION

This invention relates to lubricating compositions having as a component dithiocarbamate-containing amides.

BACKGROUND OF THE INVENTION

This invention relates various dithiocarbamate-containing amides for lubricating compositions. More specifically, this invention relates to amide compounds derived from the reaction of a dithiocarbamate compound with an amide compound containing an activated ethylenically unsaturated bond. These compounds improve extreme pressure and anti-wear properties of lubricating compositions.

U.S. Pat. No. 2,786,866 issued to Hook et al relates to dithiocarbamic derivatives used as antioxidants and anti-corrosion agents in oil compositions.

German Patent 1,178,417 relates to dithiocarbamic acid esters with strong nematocidal properties.

U.S. Pat. No. 4,064,265 issued to Varsanyi et al relates to dithiocarbamic acid esters with strong anthelmintic activity and are used to treat warm-blooded animals infected with parasitic helminths.

U.S. Pat. No. 2,535,877 issued to Stewart relates to dithiocarbamic acid esters used as plant growth regulators.

U.S Pat. No. 3,833,496 issued to Malec relates to dithiocarbamic acid esters in oil compositions as an anti-wear and anti-rust additive. Uses in lubricants and greases are disclosed.

U.S. Pat. No. 3,890,363 issued to Malec relates to carbamic acid esters as used as additives in lithium greases.

U.S. Pat. No. 4,202,832 issued to Fischer et al relates to carbamic acid esters and their use as lipid-lowering agents.

U.S. Pat. No. 4,254,142 issued to Anderson et al relates to dithiocarbamic acid ester used as immuno regulatory agents.

Great Britain Patent 1,200,491 issued to Lund relates to dithiocarbamic acid ester used in cloth treatments.

U.S. Pat. No. 2,710,872 to Thompson relates to dithiocarbamic acid esters which have medicinal, bactericidal and insecticidal character.

U.S. Pat. No. 4,758,362 issued to Butke relates to carbamate additives for lubricating compositions.

As evidenced by the foregoing, many dithiocarbamic acid derivatives have been the subject of patents. However, one must bear in mind that a slight change of chemical structure, which has even a minor increase in performance, may have significant commercial implications.

SUMMARY OF THE INVENTION

The invention relates to dithiocarbamate-containing amides of the following formula (I):

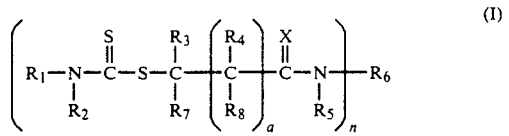

wherein $R_1$ is hydrogen or hydrocarbyl; $R_2$ is hydrocarbyl having at least 4 carbon atoms or together with $R_2$ forms a heterocyclic radical, wherein $R_3$, $R_4$, $R_7$ and $R_8$ are each independently hydrogen or alkyl;

wherein a is 0 or 1;

wherein n is 1, 2 or 3;

wherein X is oxygen or sulfur;

wherein $R_5$ is hydrogen or hydrocarbyl; and when n is 1, $R_6$ is selected from the group consisting of

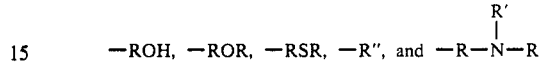

and when n is 2, $R_6$ is selected from the group consisting of

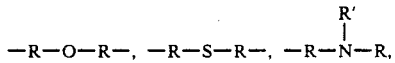

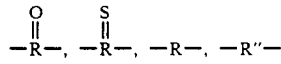

and when n is 3, $R_6$ is

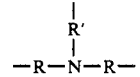

wherein R is independently an alkyl moiety, alkylene or alkylidene moiety containing 1 to 12 carbon atoms, R' is hydrogen or alkyl moiety, alkylene, alkylidene or carboxyl containing 1 to 60 carbon atoms, and R'' is aryl or substituted aryl.

An object of this invention is to provide new and useful dithiocarbamate-containing amides as well as derivatives of those amides.

An advantage of this invention is to provide lubricating compositions which have improved anti-wear and extreme pressure properties as provided by the compounds of the present invention.

A feature of the invention is that it provides an anti-wear and extreme pressure properties to lubricating compositions while not providing any metallic ash.

Another feature of the invention is that it provides anti-wear and extreme pressure properties to lubricating compositions of low or no phosphorus content.

These and other objects, advantages and features of the present invention will become apparent to those persons skilled in the art upon reading the details of the structure synthesis and usage as more fully set forth below. Reference being made to the accompanying general structural formulae forming a part hereof wherein like symbols refer to like molecular moieties throughout.

DETAILED DESCRIPTION

Before the present dithiocarbamate-containing amides and process for making such are described, it is to be understood that this invention is not limited to the particular amides or processes described as such compounds and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "an amine" includes mixtures of amines, reference to "a dithiocarbamate-containing amide" includes reference to mixtures of such amides, reference to "an aldehyde" includes mixtures of aldehydes and so forth.

The invention relates to dithiocarbamate-containing amides of the following formula (I):

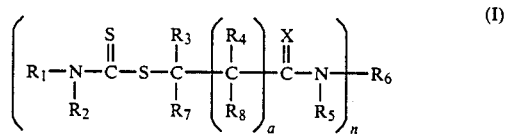

wherein $R_1$ is hydrogen or hydrocarbyl; $R_2$ is hydrocarbyl having at least 4 carbon atoms or together with $R_1$ forms a heterocyclic radical,
wherein $R_3$, $R_4$, $R_7$ and $R_8$ are each independently hydrogen or alkyl;
wherein a is 0 or 1;
wherein n is 1, 2 or 3;
wherein X is oxygen or sulfur, but preferably oxygen;
wherein $R_5$ is hydrogen or hydrocarbyl; and
when n is 1, $R_6$ is selected from the group consisting of

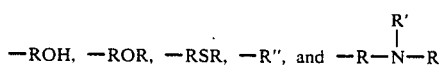

and when n is 2, $R_6$ is selected from the group consisting of

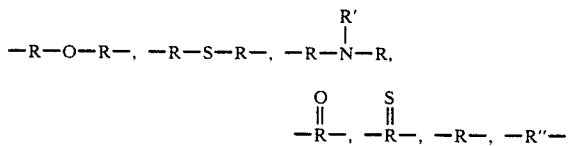

and when n is 3, $R_6$ is

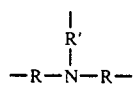

wherein R is independently an alkyl moiety, alkylene or alkylidene moiety containing 1 to 12 carbon atoms, preferably 1 to 4 carbon atoms, R' is hydrogen or alkyl moiety, alkylene, alkylidene or carboxyl containing 1 to 60 carbon atoms, and R" is aryl or substituted aryl.

In formula (I) and elsewhere in the disclosure hydrocarbyl means "hydrocarbon-based." As used herein, the term "hydrocarbon-based," "hydrocarbon-based substituent" and the like denotes a substituent having a carbon directly attached to the remainder of the molecule and having predominantly hydrocarbyl character within the context of this invention.

Examples of hydrocarbyl substituents which might be useful in connection with the present invention include the following:

(1) hydrocarbon substituents, that is, aliphatic (e.g., alkyl or alkenyl), alicyclic (e.g., cycloalkyl, cycloalkenyl) substituents, aromatic, aliphatic and alicyclic-substituted aromatic nuclei and the like as well as cyclic substituents wherein the ring is completed through another portion of the molecule (that is, for example, any two indicated substituents may together form an alicyclic radical);

(2) substituted hydrocarbon substituents, that is, those substituents containing nonhydrocarbon radicals which, in the context of this invention, do not alter the predominantly hydrocarbon substituent; those skilled in the art will be aware of such radicals (e.g., halo (especially chloro and fluoro), alkoxy, mercapto, alkylmercapto, nitro, nitroso, sulfoxy, etc.);

(3) hetero substituents, that is, substituents which will, while having predominantly hydrocarbyl character within the context of this invention, contain other than carbon present in a ring or chain otherwise composed of carbon atoms. Suitable heteroatoms will be apparent to those of ordinary skill in the art and include, for example, sulfur, oxygen, nitrogen and such substituents as, e.g., pyridyl, furyl, thienyl, imidazolyl, etc., are exemplary of these hereto substituents. Heteroatoms and preferably no more than one, will be present for each ten carbon atoms in the hydrocarbon-based substituents. Typically, there will be no such radicals or heteroatoms in the hydrocarbon-based substituent and it will, therefore, be purely hydrocarbon.

The products of the present invention may be made by the reaction of a dithiocarbamic acid or salt with an amide compound containing an ethylenically unsaturated bond.

The dithiocarbamic acid is represented by the following formula (II):

In formula (II), $R_1$ may be hydrogen or hydrocarbyl. $R_1$ is preferably alkyl having from 1 to 30 carbon atoms; more preferably 4 to 18 carbon atoms. $R_2$ may be hydrocarbyl having at least 4 carbon atoms or together with $R_1$ forms a heterocyclic radical. $R_2$ is preferably an alkyl radical having from 4 to 30 carbon atoms; more preferably 4 to 18 carbon atoms. $R_2$ must have at least 4 carbon atoms to provide that the invention is oil soluble.

The dithiocarbamic acid may be prepared by reacting carbon disulfide with amines. The amines may be primary or secondary, provided that there is sufficient number of carbon atoms to make the compound oil soluble or dispersible. In the following list of amines, the amine represents both the primary, as well as secondary amines. For instance, decylamine is understood to include didecyl amine. Non-limiting examples of amines include butylamine, hexylamine, octylamine, dodecylamine, cocoamine, and soya amine. This invention also encompasses mixed substituted amines, i.e., N-butylhexylamine, N-octyldodecylamine and the like.

The dithiocarbamic acid may be prepared by known reactions of carbon disulfide and amines. The reaction may be performed under basic conditions so that the dithiocarbamate salt is formed. A typical reaction may be reacting carbon disulfide with an amine at a temperature between 15° C. to 50° C. in the presence of an alkali base, e.g., sodium hydroxide, potassium hydroxide, etc.

Alternatively, the reaction of the carbon disulfide and amines may be performed in the presence of an amide with ethylenically unsaturated bonds. The dithiocarbamic acid is formed in situ and then reacts directly with the double bond on the amide.

The amide with ethylenically unsaturated bonds is represented by the following formula (III):

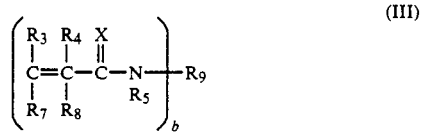

(III)

X is oxygen or sulfur, but preferably oxygen. $R_3$, $R_4$, $R_7$ and $R_8$ are each independently hydrogen or alkyl. $R_3$ and $R_4$ are preferably hydrogen. $R_7$ and $R_8$ are preferably each independently hydrogen or alkyl having from 1 to 20 carbon atoms. A more preferred alkyl range for $R_7$ and $R_8$ is from 1 to 4 carbon atoms; with 1 carbon atom most preferred. $R_5$ is hydrogen or hydrocarbyl. Preferably $R_5$ is hydrogen or alkyl having from 1 to 30 carbon atoms; more preferably $R_5$ is hydrogen or alkyl having from 3 to 5 carbon atoms; with most preferably $R_5$ is hydrogen. $R_5$ may also be hydroxyalkyl, preferably hydroxymethyl.

In formula (III), b is 1, 2 or 3. When b is 1, $R_9$ is selected from the group consisting of hydrogen,

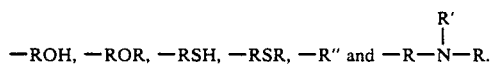

When b is 2, $R_9$ is

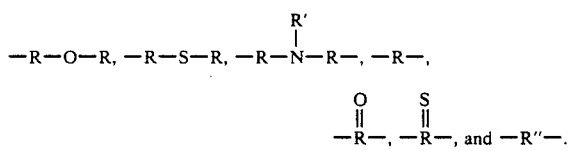

When

R, R' and R" are as defined previously.

The present invention contemplates the use of acrylamide to react with the dithiocarbamic acid as well as reacting a substituted acrylamide with the dithiocarbamic acid derivative. Examples of acrylamides which may react with the dithiocarbamic acid intermediate are acrylamide, methacrylamide, bisacrylamide, bismethacrylamide and bismethyleneacrylamide. Examples of substituted acrylamides are N-hydroxymethyl acrylamide, N-mercapto methyl acrylamide, N-(methyl, ethyl thioether) acrylamide and N-(methyl ethylether) acrylamide.

The reaction between the (II) dithiocarbamic acid and the (III) amide compound is exothermic and hence only slight heat need be applied thereto. The reaction conveniently can be carried out in an inert atmosphere such as nitrogen at from about 25° C. to about 100° C. with from about 70° C. to about 90° C. being preferred. The reaction can be carried out in the presence or absence of a solvent. Desirably, the reaction takes place in a solvent medium which typically is a hydrocarbon such as toluene, xylene, hexane, heptane, kerosene, fuel oil, an oil of a lubricating viscosity, and the like or a chlorohydrocarbon such as chloroform, carbon tetrachloride, and the like, or an alcohol such as methanol, ethanol, propanol, butanol, 2-ethylhexanol, and the like. The menstruum, in addition to acting as such, imparts favorable processing characteristics such as controlling the exothermic reaction as well as preventing unwanted side reactions. The reaction time, while dependent upon temperature, is usually as short as one or two hours or less.

A preferred embodiment of the invention is the hydroxyalkyl substituted dithiocarbamate-containing amides which are represented by the following formula:

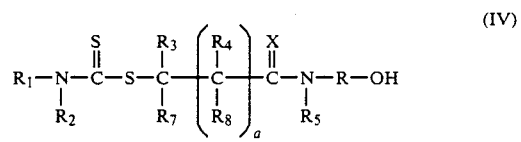

(IV)

wherein R, $R_1$, $R_2$, $R_3$, $R_4$, $R_5$, $R_7$, $R_8$, X, and a are as defined previously.

These compounds may be formed by the reaction of an amine with carbon disulfide in the presence of:
(1) an acrylamide or
(2) a hydroxyalkyl acrylamide.

The reaction of the dithiocarbamic acid or salt with N-hydroxylalkyl acrylamide occurs under basic or acidic conditions between about −5° C. to about 50° C. The N-hydroxyalkyl acrylamide is added over 3 to 20 minutes to the reaction product of an amine and carbon disulfide. The reaction usually is completed in about 1.5 to 3 hours.

When an acrylamide (1) is reacted with a dithiocarbamic acid or salt, that reaction product is further reacted with aldehydes and epoxides. The dithiocarbamic acid or salt-acrylamide reaction product reacts similarly as described above. The further reaction of the aldehydes and epoxides occurs under basic conditions at a temperature from 70° C. to 120° C. The reaction time is from about 30 minutes to 240 minutes.

Aldehydes and epoxides are useful in forming hydroxyalkyl substituted dithiocarbamate-containing amides. Examples of useful aldehydes are formaldehyde, ethanal, butanal, propanal and the like. Examples of epoxides that are useful in the present invention are epoxyethane, epoxypropane, epoxybutane and the like.

The hydroxyalkyl dithiocarbamate-containing amides may be reacted with boron containing compounds. The preferred boron-containing compounds are boric acid or borated esters. Borated esters encompass the reaction products of alcohols and epoxides with boric acid. The reaction can contain from 1 to 3 alcohols or epoxides per boron atom. The reaction occurs with no catalyst or an amine catalyst at the temperatures about 50° C. to about 100° C. A useful example of borated esters is butyl borate.

The reaction of a N-hydroxyalkyl dithiocarbamate-containing amide with boron-containing compounds occurs under either acidic or basic conditions at the temperature between about 50° C. to 150° C.

The present invention also contemplates coupled dithiocarbamate-containing amides. As shown in formula (V):

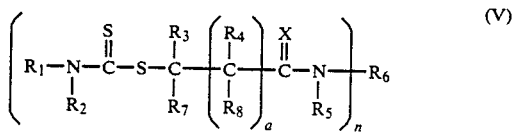

wherein $R_1$, $R_2$, $R_3$, $R_4$, $R_5$, $R_7$, $R_8$, X and are as previously described; n is 2 or 3; and $R_6$ is as previously defined in its relation to n.

A preferred embodiment of the invention includes a statistical mixture (i.e., coupled and uncoupled compounds) of the dithiocarbamate-containing amides. Any such statistical mixture is likely to include compounds of formula (I) where n = 1 as well as compound where n = 2.

The following examples are provided for those of ordinary skill in the art with a complete disclosure and description of how to make the compounds and compositions of the invention and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

EXAMPLE 1

Add dropwise 167 parts of carbon disulfide over 1.25 hours at 40° C. to a mixture of 780 parts didodecylamine, 300 parts of isopropyl alcohol and 20 parts of a 50% solution of sodium hydroxide. Maintain the reaction temperature between 25-35° C. for 1.5 hours. Raise the reaction temperature to 45° C. and maintain the temperature until $CS_2$ reflux is no longer obtained and the reaction product is a clear yellow solution. Add incrementally over one hour 142 parts of acrylamide to the reaction. Raise the reaction temperature to 70° C and maintain the temperature for 3 hours. Apply a 5 mm vacuum and raise the reaction temperature to 155° C. Filter the residue through diatomaceous earth. At room temperature add 307 parts of the filtered product to 6 parts of a 50% solution of sodium hydroxide and 16.5 parts of paraformaldehyde. Raise the reaction temperature to 90-100° C. for one hour. Apply a 5 mm vacuum and remove distillate as the temperature is raised to 115° C. Filter the residue through diatomaceous earth.

EXAMPLE 2

At 40° C. add dropwise 76 parts of carbon disulfide over 0.75 hour to a mixture of 129 parts dibutylamine, 150 parts isopropyl alcohol and 10 parts of a 50% solution of sodium hydroxide. Maintain the reaction temperature between 25-40° C. for 1.5 hours. Raise the reaction temperature to 50° C. while adding incrementally 101 parts of N-hydroxymethyl acrylamide over one hour. Raise the reaction temperature 70° C. and maintain the temperature for 3 hours. Apply a 5 mm vacuum and raise the reaction temperature to 130° C. The residue is filtered through diatomaceous earth. The filtrate is the product.

EXAMPLE 3

At 40° C. add dropwise 76 parts of carbon disulfide over 0.75 hour to a mixture of 129 parts of dibutylamine and 150 parts of isopropyl alcohol. Maintain the reaction temperature between 25-40° C. for 1.5 hours. When the reaction mixture is a clear yellow solution, add 71 parts of acrylamide incrementally over one hour. Raise the reaction temperature to 70° C. and maintain the temperature for 3 hours. Apply a 5 mm vacuum and raise the temperature to 155° C. Cool the residue to room temperature and add 33 parts of paraformaldehyde. Raise the reaction temperature to 90-100° C. under nitrogen and maintain the temperature for one hour. Apply a 5 mm vacuum while raising the reaction temperature to 115° C. Filter the residue through diatomaceous earth. The filtrate is the product.

EXAMPLE 4

At 40° C. add dropwise 167 parts of carbon disulfide over 1.25 hours to a mixture of 780 parts of didodecylamine and 300 parts of isopropyl alcohol. Maintain the reaction temperature between 25-35° C. for 1.5 hours, then raise the reaction temperature to 45° C. Maintain the reaction temperature at 45° C. until no carbon disulfide reflux is obtained and the reaction product is a clear yellow solution. Raise the reaction temperature to 50° C. while adding incrementally 202 parts of N-hydroxymethyl acrylamide over one hour. Raise the reaction temperature to 70° C. and maintain the temperature for 3 hours. Apply a 5 mm vacuum while raising the temperature to 155° C. Filter the residue through diatomaceous earth. The filtrate is desired product.

EXAMPLE 5

Add 31 parts boric acid over 2 hours to 573 parts of the product of EXAMPLE 1. Gradually raise the reaction temperature to 100° C. while distilling with a nitrogen sparge. Add 150 parts of diluent oil to the product and apply a 5 mm vacuum while raising the temperature to 155° C. Filter the residue through diatomaceous earth. The filtrate is the desired product.

EXAMPLE 6

Add 31 parts of boric acid over 2 hours to 309 parts of the product of EXAMPLE 4. Gradually raise the temperature to 100° C. while distilling with a nitrogen sparge. Add 100 parts of a diluent oil to the product and apply a 5 mm vacuum while heating the reaction to 155° C. Filter the residue through diatomaceous earth, the filtrate is the desired product.

EXAMPLE 7

At 40° C. add dropwise over 1.25 hours 152 parts of carbon disulfide to a mixture of 780 parts of didodecylamine and 300 parts of isopropyl alcohol. Maintain the reaction temperature at between 25-35° C. for 1.5 hours. Maintain the reaction temperature at 45° C. until no carbon disulfide reflux is visible. Add incrementally over one hour 142 parts of acrylamide to the reaction mixture. Raise the reaction temperature to 70° C. and hold for 3 hours. Apply a 5 mm vacuum while raising the temperature to 155° C. Cool the reaction to 40° C., and add 11 parts of para-toluene sulfonic acid, 33 parts of paraformaldehyde and 350 parts of toluene. Raise the reaction temperature to between 90-130° C. while distilling water with a nitrogen sparge. Upon cessation of water evolution cool the reaction to 110° C. and apply a 15 mm vacuum to remove the solvent. Filter the residue through diatomaceous earth, the filtrate is the desired product.

EXAMPLE 8

At 40° C. add 152 parts of carbon disulfide dropwise over one hour to a mixture of 780 parts of didodecylamine and 1300 parts of isopropyl alcohol. Maintain the reaction temperature between 25-35° C. for 1.5 hours. Raise the reaction temperature to 45° C. and add 101 parts of N-hydroxymethyl acrylamide and 71 parts acrylamide. Maintain the reaction temperature at 45° C. for 1.5 hours. Add 11 parts para-toluene sulfonic acid to the reaction mixture and raise the temperature to 125° C. Remove distillate over 4 hours with nitrogen sparging. Apply a 15 mm vacuum to remove distillate at 120° C. Filter the residue through diatomaceous earth, the filtrate is the desired product.

The dithiocarbamate containing amides of the present invention may be used, in lubricants or in concentrates, by itself or in combination with any other known additive which includes, but is not limited to dispersants, detergents, antioxidants, anti-wear agents, extreme pressure agents, emulsifiers, demulsifiers, friction modifiers, anti-rust agents, corrosion inhibitors, viscosity improvers, pour point depressants, dyes, and solvents to improve handleability which may include alkyl and/or aryl hydrocarbons. These additives may be present in various amounts depending on the needs of the final product.

Dispersants include but are not limited to hydrocarbon substituted succinimides, succinamides, esters, and Mannich dispersants as well as materials functioning both as dispersants and viscosity improvers. The dispersants listed above may be post-treated with reagents such as urea, thiourea, carbon disulfide, aldehydes, ketones, carboxylic acids, hydrocarbon substituted succinic anhydride, nitriles, epoxides, boron compounds, phosphorus compounds and the like.

Detergents include, but are not limited to Newtonian or non-Newtonian, neutral or basic salts of alkali, alkaline earth or transition metals with one or more hydrocarbyl sulfonic acid, carboxylic acid, phosphoric acid, thiophosphoric acid, dithiophosphoric acid, phosphinic acid, thiophosphinic acid, sulfur coupled phenol or phenol. Basic salts are salts that contain a stoichiometric excess of metal present per acid function.

Antioxidants, corrosion inhibitors, extreme pressure and anti-wear agents include but are not limited to metal salts of a phosphorus acid, metal salts of a thiophosphorus acid or dithiophosphorus acid; organic sulfides and polysulfides; chlorinated aliphatic hydrocarbons; phosphorus esters including dihydrocarbyl and trihydrocarbyl phosphites; boron-containing compounds including borate esters; and molybdenum compounds.

Viscosity improvers include but are not limited to polyisobutenes, polymethyacrylate acid esters, polyacrylate acid esters, diene polymers, polyalkyl styrenes, alkenyl aryl conjugated diene copolymers, polyolefins and multifunctional viscosity improvers.

Pour point depressants are a particularly useful type of additive often included in the lubricating oils described herein. See for example, page 8 of "Lubricant Additives" by C. V. Smalheer and R. Kennedy Smith (Lesius-Hiles Company Publishers, Cleveland, Ohio, 1967).

Anti-foam agents used to reduce or prevent the formation of stable foam include silicones or organic polymers. Examples of these and additional anti-foam compositions are described in "Foam Control Agents", by Henry T. Kerner (Noyes Data Corporation, 1976), pages 125-162.

These and other additives are described in greater detail in U.S. Pat. No. 4,582,618 (column 14, line 52 through column 17, line 16, inclusive), herein incorporated by reference for its disclosure of other additives that may be used in combination with the present invention.

The concentrate might contain 0.01 to 90% by weight of the amides. The amides may be present in a final product, blend or concentrate in (in a minor amount, i.e, up to 50% by weight) any amount effective to act as an anti-wear agent, but is preferably present in oil of lubricating viscosity, hydraulic oils, fuel oils, gear oils or automatic transmission fluids in an amount of from about 0.5 to about 10%, preferably 0.1 to about 5% by weight, most preferably 1% to about 5%.

The lubricating compositions and methods of this invention employ an oil of lubricating viscosity, including natural or synthetic lubricating oils and mixtures thereof. Natural oils include animal oils, vegetable oils, mineral lubricating oils, solvent or acid treated mineral oils, and oils derived from coal or shale. Synthetic lubricating oils include hydrocarbon oils, halo-substituted hydrocarbon oils, alkylene oxide polymers, esters of dicarboxylic acids and polyols, esters of phosphorus-containing acids, polymeric tetrahydrofurans and silcon-based oils.

Unrefined, refined and rerefined oils, either natural or synthetic may be used in the compositions of the present invention.

Specific examples of the oils of lubricating viscosity are described in U.S. Pat. No. 4,326,972 and European Patent Publication 107,282, both herein incorporated by reference for their disclosures relating to lubricating oils. A basic, brief description of lubricant base oils appears in an article by D. V. Brock, "Lubricant Engineering", volume 43, pages 184-185, March, 1987. This article is herein incorporated by reference for its disclosures relating to lubricating oils.

A description of oils of lubricating viscosity occurs in U.S. Pat. No. 4,582,618 (column 2, line 37 through column 3, line 63, inclusive), herein incorporated by reference for its disclosure to oils of lubricating viscosity.

A lubricating composition may be prepared by adding 0.1 to 10% of any one of the products of Examples 1-8 to an oil.

A concentrate composition may be prepared by adding from 0.01 to 90% of any one of the products of Examples 1-8 to an oil.

A grease composition may be prepared by adding 0.1% to 50% of any one of the products of Examples 1-8 to a grease composition or base grease stock.

An aqueous fluid may be prepared by adding 0.1% to 20% of any one of the products of Examples 1-8 to water in the presence of an emulsifying agent or a coupling agent.

The instant invention is shown and described herein in what is considered to be the most practical, and the preferred embodiments. It is recognized, however, that departures may be made therefrom which are within the scope of the invention, and that obvious modifications will occur to one skilled in the art upon reading this disclosure.

What is claimed is:

1. A compound, comprising a compound represented by formula (I):

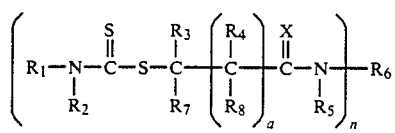 (I)

wherein $R_1$ is hydrogen or hydrocarbyl; and $R_2$ is hydrocarbyl having at least 4 carbon atoms,
wherein $R_3$, $R_4$, $R_7$ and $R_8$ are each independently hydrogen or alkyl;
wherein a is 0 or 1;
wherein n is 1, or 2;
wherein X is oxygen;
wherein $R_5$ is hydrogen or hydrocarbyl; and
when n is 1, $R_6$ is —R″
and when n is 2, $R_6$ is selected from the group consisting of —R—O—R—, —R—, —R″—
wherein R is independently an alkyl moiety, alkylene or alkylidene moiety containing 1 to 12 carbon atoms, and R″ is aryl or substituted aryl.

2. The compound as claimed in claim 1, wherein $R_1$ and $R_2$ are both alkyl having from 4 to 12 carbon atoms.

3. The compound as claimed in claim 1, wherein $R_5$ is hydrogen.

4. The compound as claimed in claim 1, wherein $R_5$ is alkyl.

5. The compound as claimed in claim 1, wherein n is 2 and $R_6$ is methylene.

6. The compound as claimed in claim 1, wherein $R_7$ and $R_8$ are each independently hydrogen or methyl.

7. The compound as claimed in claim 5, wherein $R_3$, $R_4$, $R_5$, $R_7$ and $R_8$ are each hydrogen.

8. A compound having the formula

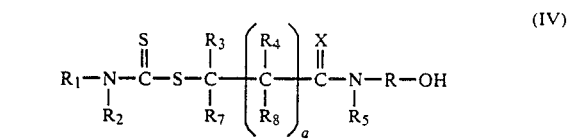 (IV)

wherein $R_1$ is hydrogen or hydrocarbyl; $R_2$ is hydrocarbyl having at least 4 carbon atoms; $R_3$, $R_4$, $R_7$ and $R_8$ are each independently hydrogen or alkyl; a is 0 or 1; X is oxygen or sulfur; $R_5$ is hydrogen or hydrocarbyl; and R has 2, 3 or 4 carbon atoms.

9. The compound of claim 8, wherein $R_5$ is hydrogen or alkyl.

10. The compound of claim 8, wherein $R_7$ and $R_8$ are independently hydrogen or methyl.

11. The compound of claim 8, wherein $R_1$ ad $R_2$ are independently alkyl, having 4 to 12 carbon atoms.

12. The compound of claim 8, wherein $R_3$ and $R_4$ are hydrogen.

* * * * *